US005966500A

United States Patent [19]

Wollam

[11] Patent Number: 5,966,500

[45] Date of Patent: Oct. 12, 1999

[54] HOUSEHOLD SMOKE GENERATOR

[76] Inventor: Ryan M. Wollam, 1730 W. 13th St., Dalles, Oreg. 97058

[21] Appl. No.: 09/168,462

[22] Filed: Oct. 8, 1998

[51] Int. Cl.[6] .......................... A61M 16/00; A01G 13/06

[52] U.S. Cl. .......................................... 392/390; 392/386

[58] Field of Search .................................. 392/386, 390, 392/391, 392, 397, 398, 403, 404, 405, 400; 261/139, DIG. 65; 122/459, 461, 462

[56] References Cited

U.S. PATENT DOCUMENTS 5,023,020 6/1991 Machinda et al. .................... 261/18.1
5,805,768 9/1998 Schwartz et al. ....................... 392/390

*Primary Examiner*—Teresa Walberg
*Assistant Examiner*—Sam Paik

[57] ABSTRACT

A smoke generating system is provided for making a household appear inhabited. The household is equipped with an outlet. Next provided is a smoke generator for generating smoke and expelling the same from the outlet of the household.

19 Claims, 2 Drawing Sheets

HOUSEHOLD SMOKE GENERATOR

BACKGROUND OF THE INVENTION

1. Field of the Invention

The present invention relates to smoke generators and more particularly pertains to a new household smoke generator for abating the threat of a burglary of a household by simulating inhabitation.

2. Description of the Prior Art

The use of smoke generators is known in the prior art. More specifically, smoke generators heretofore devised and utilized are known to consist basically of familiar, expected and obvious structural configurations, notwithstanding the myriad of designs encompassed by the crowded prior art which have been developed for the fulfillment of countless objectives and requirements.

Known prior art smoke generators include U.S. Pat. No. 4,779,525; U.S. Pat. No. 5,259,318; U.S. Pat. No. 5,048,545; U.S. Pat. No. 4,580,583; U.S. Pat. No. 4,198,574; and U.S. Pat. No. Des. 315,617.

In these respects, the household smoke generator according to the present invention substantially departs from the conventional concepts and designs of the prior art, and in so doing provides an apparatus primarily developed for the purpose of abating the threat of a burglary of a household by simulating inhabitation.

SUMMARY OF THE INVENTION

In view of the foregoing disadvantages inherent in the known types of smoke generators now present in the prior art, the present invention provides a new household smoke generator construction wherein the same can be utilized for abating the threat of a burglary of a household by simulating inhabitation.

The general purpose of the present invention, which will be described subsequently in greater detail, is to provide a new household smoke generator apparatus and method which has many of the advantages of the smoke generators mentioned heretofore and many novel features that result in a new household smoke generator which is not anticipated, rendered obvious, suggested, or even implied by any of the prior art smoke generators, either alone or in any combination thereof.

To attain this, the present invention generally comprises a tubular stove pipe having an interior end situated within a household. The stove pipe further includes an exterior end extending from the household for excreting smoke upon the receipt thereof from the interior end. As shown in FIG. 1, an ash can is provided having a vertically oriented cylindrical configuration with a circular aperture formed on a top face thereof. Also included is a central housing including a front extent with a rectangular configuration. The front extent of the housing is formed of a front face, a rear face, a top face and a pair of side faces defining an open bottom. The central housing further includes a bottom extent with a peripheral side wall having a top edge mounted to a periphery of the open bottom of the front extent. The peripheral side wall of the bottom extent extends downwardly from the front extent of the housing with a rear wall and a pair of side walls that taper inwardly. As shown in FIG. 1, the peripheral side wall of the bottom extent terminates in a vertically oriented cylindrical sleeve for being removably inserted within the aperture of the ash can. With continuing reference to FIGS. 1 & 2, the central housing further includes a rear extent with a rectangular configuration having a width ⅓ that of the front extent. A front face of the rear extent of the housing is mounted to a central extent of the front extent. Further, a top face of the rear extent extends above the front extent of the housing a predetermined height. A circular aperture is formed in such top face for releasably receiving the interior end of the stove pipe. Note FIG. 1. Also included is a pellet hopper including a planar rear face having a bottom edge mounted to a top edge of the front face of the front extent of the housing in coplanar relationship therewith. The pellet hopper is further equipped with a pair of side faces and a tapering front face for defining an open top extended above the front extent of the housing the predetermined height. A lid is hingably mounted over the open top of the pellet hopper. Further, an open bottom of the pellet hopper remains in communication with a horizontally oriented elongated slot formed in the front face of the front extent of the housing. In use, the pellet hopper serves to contain a plurality of pellets which are adapted to generate smoke upon being heated. FIG. 2 shows a heater plate with a planar rectangular configuration mounted to a periphery of the open bottom of the front extent of the housing. For reasons that will soon become apparent, the heater plate has a matrix of apertures formed therein. In operation, the heater plate is adapted to generate heat during the receipt of power. Associated therewith is a fan mounted within a hole formed between the rear face of the front extent and the front face of the rear extent of the housing. The fan circulates air from the front extent of the housing to the rear extent thereof during the receipt of power. Slidably mounted in front of the slot between the front extent of the housing and the pellet hopper is a planar rectangular door. The door has a solenoid connected thereto with an unbiased orientation for maintaining the door over the slot to preclude the passage of the pellets to the front extent of the housing. The solenoid further has a biased orientation upon the receipt of an activation signal. In such biased orientation, the solenoid functions to lower the door below the slot to allow the passage of the pellets to the front extent of the housing. Finally, a timer mechanism is connected to the heater plate, fan, and solenoid. The timer mechanism is adapted for transmitting the activation signal to the solenoid and thereafter supplying power to the heater plate and fan for a predetermined amount of time. This generates smoke which is circulated to the exterior end of the stove pipe.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein arc for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new household smoke generator apparatus and method which has many of the advantages of the smoke generators mentioned heretofore and many novel features that result in a new household smoke generator which is not anticipated, rendered obvious, suggested, or even implied by any of the prior art smoke generators, either alone or in any combination thereof.

It is another object of the present invention to provide a new household smoke generator which may be easily and efficiently manufactured and marketed.

It is a further object of the present invention to provide a new household smoke generator which is of a durable and reliable construction.

An even further object of the present invention is to provide a new household smoke generator which is susceptible of a low cost of manufacture with regard to both materials and labor, and which accordingly is then susceptible of low prices of sale to the consuming public, thereby making such household smoke generator economically available to the buying public.

Still yet another object of the present invention is to provide a new household smoke generator which provides in the apparatuses and methods of the prior art some of the advantages thereof, while simultaneously overcoming some of the disadvantages normally associated therewith.

Still another object of the present invention is to provide a new household smoke generator for abating the threat of a burglary of a household by simulating inhabitation.

Even still another object of the present invention is to provide a new household smoke generator for making a household appear inhabited. The household is equipped with an outlet. The smoke generator is adapted for generating smoke and expelling the same from the outlet of the household.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
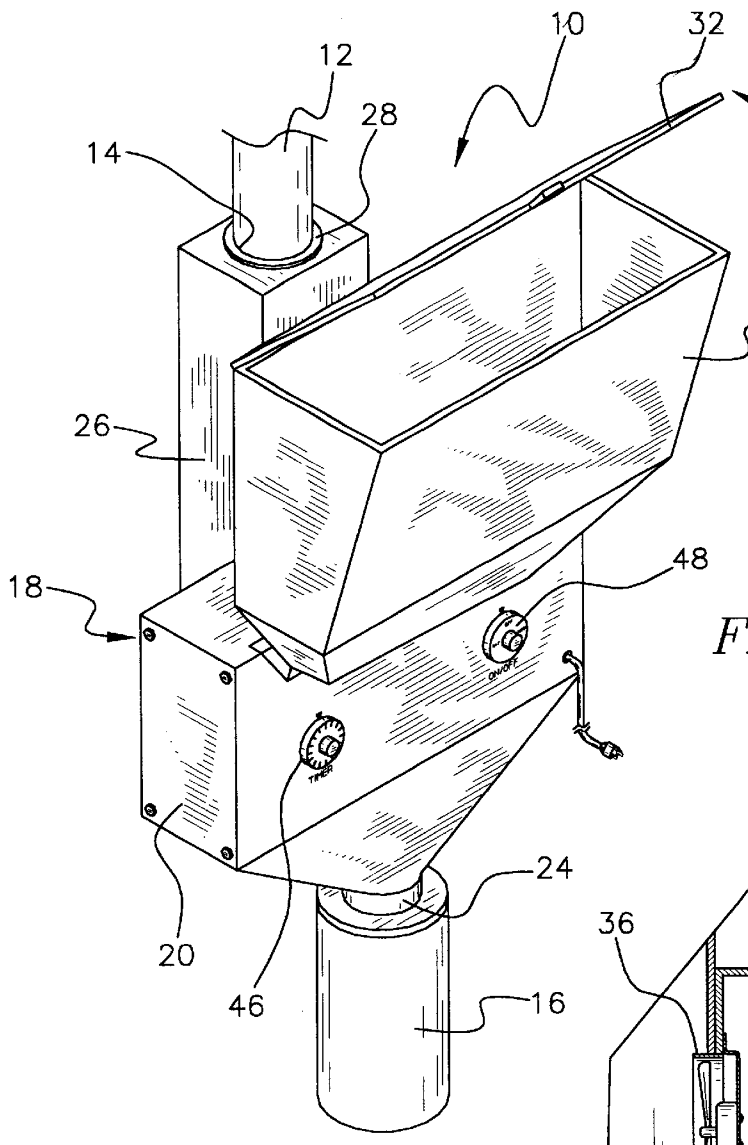
FIG. 1 is a perspective view of a new household smoke generator according to the present invention.

With reference now to the drawings, and in particular to FIGS. 1 through 4 thereof, a new household smoke generator embodying the principles and concepts of the present invention and generally designated by the reference numeral 10 will be described.

The present invention, designated as numeral 10, includes a tubular stove pipe 12 having an interior end 14 situated within a household. The stove pipe further includes an exterior end extending from the household for excreting smoke upon the receipt thereof from the interior end. As shown in FIG. 1, an ash can 16 is provided having a vertically oriented cylindrical configuration with a circular aperture formed on a top face thereof.

Also provided is a central housing 18 including a front extent 20 with a rectangular configuration. The front extent of the housing is formed of a front face, a rear face, a top face and a pair of side faces defining an open bottom. The central housing further includes a bottom extent 22 with a peripheral side wall having a top edge mounted to a periphery of the open bottom of the front extent. The peripheral side wall of the bottom extent extends downwardly from the front extent of the housing with a rear wall and a pair of side walls that taper inwardly. As shown in FIG. 1, the peripheral side wall of the bottom extent terminates in a vertically oriented cylindrical sleeve 24 for being removably inserted within the aperture of the ash can.

With continuing reference to FIGS. I & 2, the central housing further includes a rear extent 26 with a rectangular configuration having a width 1/3 that of the front extent. A front face of the rear extent of the housing is mounted to a central portion of the front extent. Further, a top face of the rear extent extends above the front extent of the housing a predetermined height. A circular aperture 28 is formed in such top face for releasably receiving the interior end of the stove pipe. Note FIG. 1.

Also included is a pellet hopper 30 including a planar rear face having a bottom edge mounted to a top edge of the front face of the front extent of the housing in coplanar relationship therewith. The pellet hopper is further equipped with a pair of side faces and a tapering front face for defining an open top extended above the front extent of the housing the predetermined height. A lid 32 is hingably mounted over the open top of the pellet hopper. Further, an open bottom of the pellet hopper remains in communication with a horizontally oriented elongated slot formed in the front face of the front extent of the housing. In use, the pellet hopper serves to contain a plurality of pellets which are adapted to generate smoke upon being heated. The pellets used in the present invention are similar to those used with pellet-style stoves and the like.

Figure 2:
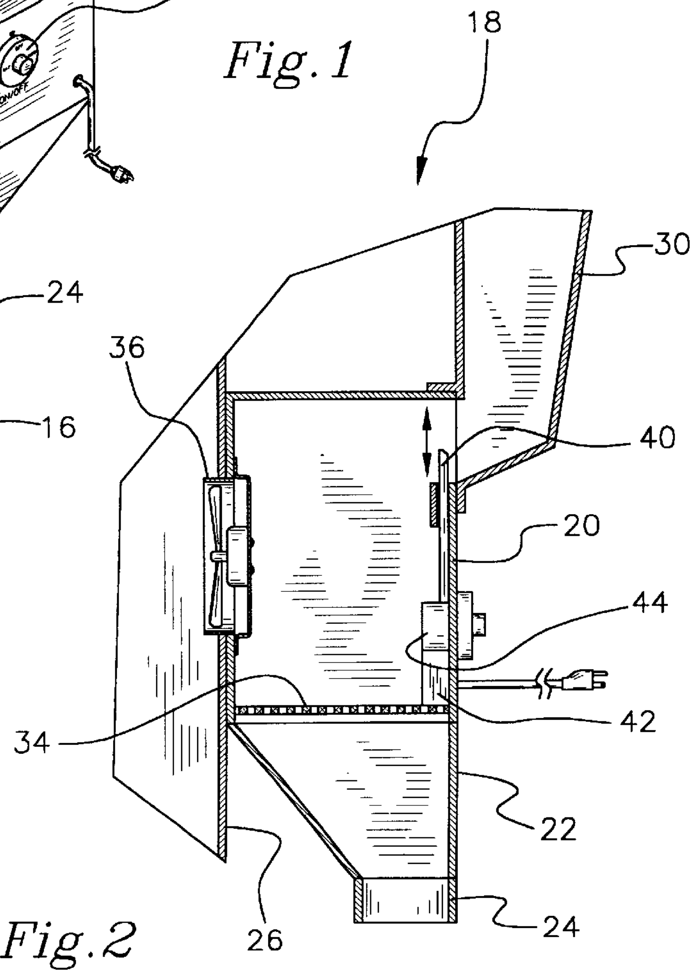
FIG. 2 is a side cross-sectional view of the present invention.

FIG. 2 shows a horizontally oriented heater plate 34 with a planar rectangular configuration mounted to a periphery of the open bottom of the front extent of the housing. For reasons that will soon become apparent, the heater plate has a matrix of apertures formed therein. In operation, the heater plate is adapted to generate heat during the receipt of power.

Associated therewith is a fan 36 mounted within a hole formed between the rear face of the front extent and the front face of the rear extent of the housing. The fan circulates air from the front extent of the housing to the rear extent thereof during the receipt of power.

Slidably mounted in front of the slot between the front extent of the housing and the pellet hopper is a planar rectangular door 40. The door has a solenoid 42 connected thereto with an unbiased orientation for maintaining the door over the slot to preclude the passage of the pellets to the front extent of the housing. The solenoid further has a biased orientation for a short period of time upon the receipt of an activation signal. In such biased orientation, the solenoid functions to lower the door below the slot to allow the passage of the pellets to the front extent of the housing.

Finally, a timer mechanism 44 is connected to the heater plate, fan, and solenoid. The timer mechanism is adapted for transmitting the activation signal to the solenoid and thereafter supplying power to the heater plate and fan for a predetermined amount of time. Such predetermined amount of time is preferably user-selected via a first dial 46. The frequency in which the timer mechanism carries out the foregoing operation is preferably user-selected by way of a second dial 48. Choices of frequency may range between a day and a week depending on a length of time an owner of the household plans to leave. As an option, the present invention may be manually actuated. The present invention thus generates smoke which is circulated to the exterior end of the stove pipe, thereby abating the threat of a burglary by simulating inhabitation.

Figure 3:
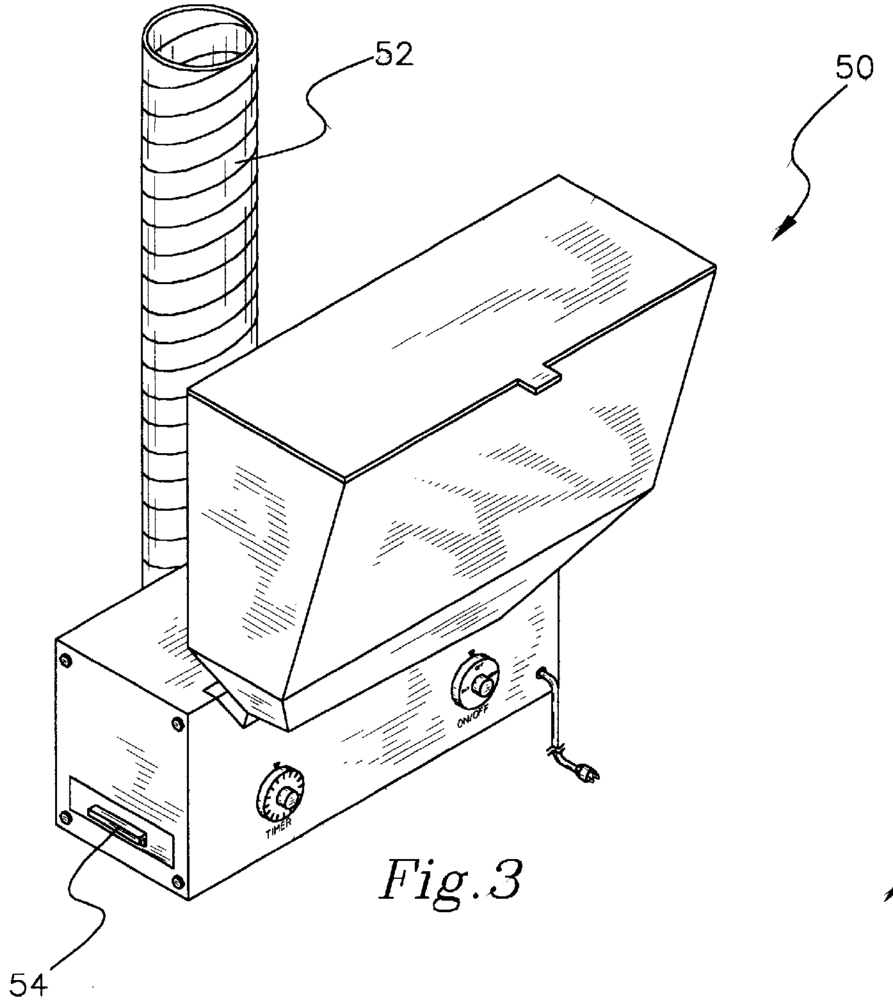
FIG. 3 is a perspective view of another embodiment of the present invention.
Figure 4:
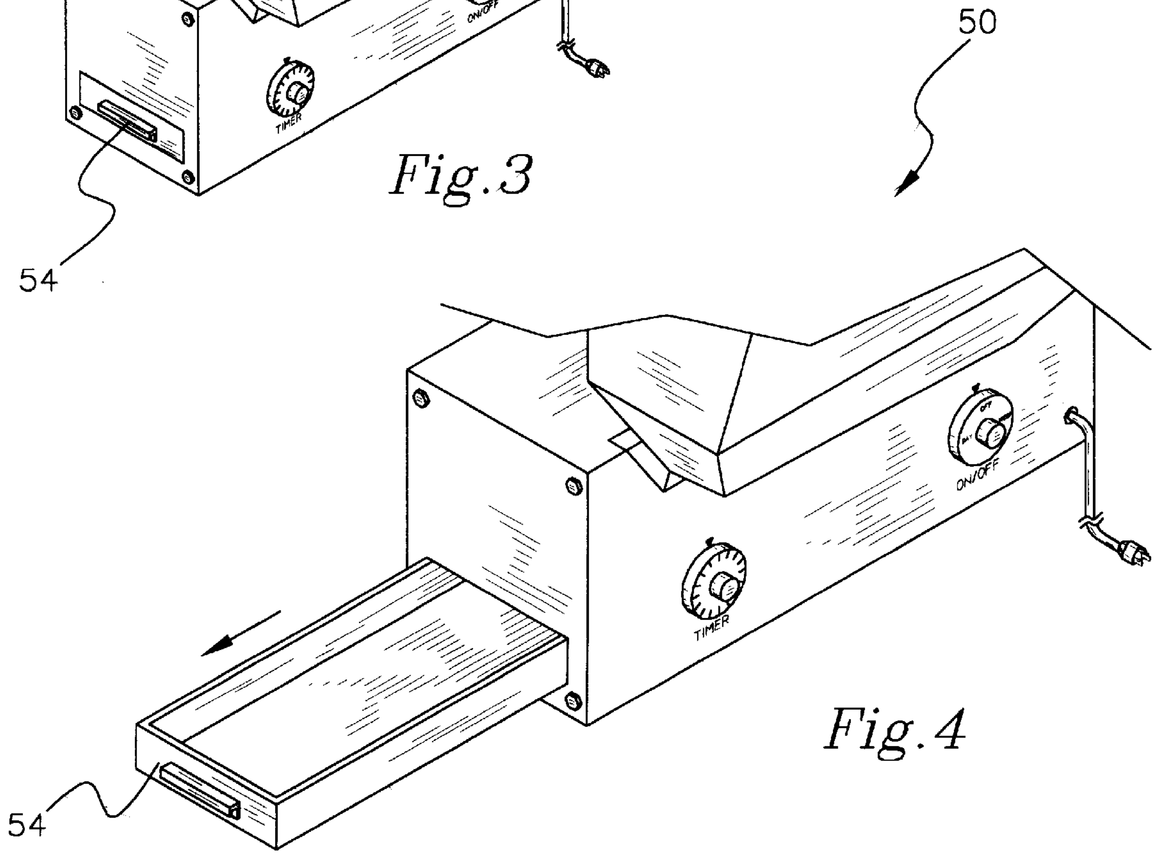
FIG. 4 is another perspective view of the embodiment of the present invention shown in FIG. 3 with the tray thereof in an extended orientation.

In an alternate embodiment 50, shown in FIGS. 3 & 4, the present invention is specifically designed to accommodate a fire place and chimney. In particular, the housing of the present embodiment is equipped with a flexible pipe 52 for directing the smoke into the chimney. Further, a removable tray 54 is employed in lieu of the ash can of the previous embodiment.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A smoke generating device for making a household to appear inhabited comprising, in combination:

a tubular stove pipe having an interior end situated within a household and an exterior end extending from the household for excreting smoke upon the receipt thereof from the interior end;

an ash can having a vertically oriented cylindrical configuration with a circular aperture formed on a top face thereof;

a central housing including a front extent with a rectangular configuration formed of a front face, a rear face, a top face and a pair of side faces defining an open bottom, the central housing further including a bottom extent with a peripheral side wall having a top edge mounted to a periphery of the open bottom of the front extent and extending downwardly with a rear wall and a pair of side walls that taper inwardly, the peripheral side wall of the bottom extent terminating in a vertically oriented cylindrical sleeve for being removably inserted within the aperture of the ash can, the central housing further including a rear extent with a rectangular configuration with a width ⅓ that of the front extent, a front face mounted to a central extent of the front extent, and a top face which extends above the front extent of the housing a predetermined height and has a circular aperture formed therein for releasably receiving the interior end of the stove pipe;

a pellet hopper including a planar rear face having a bottom edge mounted to a top edge of the front face of the front extent of the housing in coplanar relationship therewith, a pair of side faces and a tapering front face for defining an open top extended above the front extent of the housing the predetermined height with a lid hingably mounted thereon and an open bottom in communication with a horizontally oriented elongated slot formed in the front face of the front extent of the housing, the pellet hopper adapted to contain a plurality of pellets adapted to generate smoke upon being heated;

a heater plate with a planar rectangular configuration mounted to a periphery of the open bottom of the front extent of the housing, the heater plate having a matrix of apertures formed therein, wherein the heater plate is adapted to generate heat during the receipt of power;

a fan mounted within a hole formed between the rear face of the front extent and the front face of the rear extent of the housing, the fan adapted to circulate air from the front extent of the housing to the rear extent thereof during the receipt of power;

a planar rectangular door slidably mounted in front of the slot between the front extent of the housing and the pellet hopper, the door having a solenoid connected thereto with an unbiased orientation for maintaining the door over the slot to preclude the passage of the pellets to the front extent of the housing, the solenoid further having a biased orientation upon the receipt of an activation signal for lowering the door below the slot to allow the passage of the pellets to the front extent of the housing; and a timer mechanism connected to the heater plate, fan, and solenoid for transmitting the activation signal to the solenoid and thereafter supplying power to the heater plate and fan for a predetermined amount of time, thereby generating smoke which is circulated to the exterior end of the stove pipe.

2. A smoke generating system for making a household appear inhabited comprising:

a household with an outlet;

a housing in communication with the outlet; and a smoke generator located in the housing for generating smoke, the housing being adapted for directing the smoke generated by the smoke generator to the outlet of the household;

wherein the outlet of the household is a component of a chimney of the household.

3. The smoke generating system as set forth in claim 2 wherein the outlet is a component of a stove pipe which is removably attached with respect to the housing.

4. The smoke generating system as set forth in claim 2 wherein the smoke generator includes a fan for circulating the smoke from the outlet of the household.

5. The smoke generating system as set forth in claim 2 wherein the smoke generator includes a heater for heating pellets which generate smoke upon being heated.

6. The smoke generating system as set forth in claim 5 wherein the heater is a horizontally oriented plate with a matrix of apertures for allowing ash from the pellets to be deposited within an ash can positioned therebelow.

7. The smoke generating system as set forth in claim 5 wherein the heater is a horizontally oriented plate with a matrix of apertures for allowing ash from the pellets to be deposited within an ash tray.

8. A smoke generating system as set forth in claim 5 wherein the heater is controlled by way of a timer.

9. A smoke generating system as set forth in claim 5 and further including a pellet hopper with a door for selectively dispensing the pellets to the heater.

10. A smoke generating system as set forth in claim 9 wherein the door is controlled by way of a timer.

11. A smoke generating system as set forth in claim 2 wherein the smoke generator is controlled by way of a timer.

12. A smoke generating device for generating smoke to be expelled from a chimney of a house, the smoke generating device comprising:

a housing including a conduit adapted for connection to the chimney of a house such that the conduit is in communication with the chimney; and a smoke generator located in the housing for generating smoke, the smoke generator being in communication with the conduit of the housing such that smoke generated by the smoke generator may be directed to the chimney of the house.

13. The smoke generating device as set forth in claim 12 wherein the conduit is a stove pipe which is removably attached to the housing.

14. The smoke generating device as set forth in claim 12 wherein the smoke generator includes a fan for moving the smoke generated by the smoke generator through the conduit to a chimney of a house.

15. The smoke generating device as set forth in claim 12 wherein the smoke generator includes a heater for heating pellets which generate smoke upon being heated.

16. A smoke generating device as set forth in claim 15 wherein the heater is controlled by way of a timer.

17. A smoke generating device as set forth in claim 15 and further including a pellet hopper with a door for selectively dispensing the pellets to the heater.

18. A smoke generating device as set forth in claim 17 wherein the door is controlled by way of a timer.

19. A smoke generating device as set forth in claim 12 wherein the smoke generator is controlled by way of a timer.

* * * * *